United States Patent
Williams et al.

(10) Patent No.: US 9,296,606 B2
(45) Date of Patent: Mar. 29, 2016

(54) MEMS DEVICE WITH A STRESS-ISOLATION STRUCTURE

(71) Applicant: INVENSENSE, INC., San Jose, CA (US)

(72) Inventors: Kirt Reed Williams, Portola Valley, CA (US); Matthew Julian Thompson, Beaverton, OR (US); Joseph Seeger, Menlo Park, CA (US)

(73) Assignee: INVENSENSE, INC., San Jose, CA (US)

( * ) Notice: Subject to any disclaimer, the term of this patent is extended or adjusted under 35 U.S.C. 154(b) by 137 days.

(21) Appl. No.: 14/172,894

(22) Filed: Feb. 4, 2014

(65) Prior Publication Data
US 2015/0284239 A1 Oct. 8, 2015

(51) Int. Cl.
*G01P 15/08* (2006.01)
*B81B 3/00* (2006.01)
*G01N 3/20* (2006.01)
*G01P 15/125* (2006.01)
*B81C 1/00* (2006.01)
*G01K 1/00* (2006.01)

(52) U.S. Cl.
CPC ............ *B81B 3/0051* (2013.01); *B81C 1/00666* (2013.01); *G01K 1/00* (2013.01); *G01N 3/20* (2013.01); *G01P 15/125* (2013.01); *B81B 2201/0221* (2013.01); *B81B 2201/0235* (2013.01); *B81B 2201/0271* (2013.01)

(58) Field of Classification Search
CPC ................... H01L 2924/00; H01L 2924/1461; H01L 2224/73265; H01L 29/84; B81B 2201/0264; B81B 2201/0235; G01P 15/125
See application file for complete search history.

(56) References Cited

U.S. PATENT DOCUMENTS

| | | | |
|---|---|---|---|
| 2004/0219340 A1* | 11/2004 | McNeil et al. | 428/209 |
| 2009/0031809 A1* | 2/2009 | Lin et al. | 73/514.32 |
| 2014/0026660 A1* | 1/2014 | Zhang et al. | 73/504.12 |
| 2014/0167189 A1* | 6/2014 | Steimle et al. | 257/415 |

* cited by examiner

*Primary Examiner* — Shaun Campbell
(74) *Attorney, Agent, or Firm* — Minisandram Law Firm; Raghunath S. Minisandram

(57) ABSTRACT

A method and system for a MEMS device is disclosed. The MEMS device includes a free layer, with a first portion and a second portion. The MEMS device also includes a underlying substrate, the free layer movably positioned relative to the underlying substrate. The first portion and second portion of the free layer are coupled through at least one stem. A sense material is disposed over portions of the second portion of the free layer. Stress in the sense material and second portion of the free layer does not cause substantial deflection of the first portion.

65 Claims, 11 Drawing Sheets

MEMS DEVICE WITH A STRESS-ISOLATION STRUCTURE

TECHNICAL FIELD

The present invention relates generally to microelectromechanical systems (MEMS) device and more particularly, to a MEMS device with a stress isolation structure.

DESCRIPTION OF RELATED ART

MEMS devices are formed using various semiconductor manufacturing processes. MEMS devices may have fixed and movable portions. MEMS force sensors have one or more sense material, which react to an external influence imparting a force onto the movable portions. The sense material can be the MEMS structural layer or a deposited layer. The MEMS force sensor may be configured to measure these movements induced by the external influence to determine the type and extent of the external influence.

Sometimes, large external acceleration or shock may impart undesirable movements of the movable portions. These undesirable movements may induce false measurements or introduce errors into the measurement capabilities of the MEMS device. It may be desirable to minimize the impact of extraneous forces or stress on operation of the MEMS device.

With these needs in mind, the current disclosure arises. This brief summary has been provided so that the nature of the disclosure may be understood quickly. A more complete understanding of the disclosure can be obtained by reference to the following detailed description of the various embodiments thereof in connection with the attached drawings.

SUMMARY OF THE INVENTION

In one embodiment, a MEMS device is disclosed. The MEMS device includes a free layer, with a first portion and a second portion. The MEMS device also includes an underlying substrate, the free layer movably positioned relative to the underlying substrate. The first portion and second portion of the free layer are coupled through at least one stem. A sense material is disposed over portions of the second portion of the free layer.

In yet another embodiment, a method for providing a MEMS device is disclosed. MEMS device includes a free layer, with a first portion and a second portion. The MEMS device also includes a underlying substrate, the free layer movably positioned relative to the underlying substrate. The first portion and the second portion of the free layer are coupled through at least one stem. A sense material is disposed over portions of the second portion of the free layer.

This brief summary is provided so that the nature of the disclosure may be understood quickly. A more complete understanding of the disclosure can be obtained by reference to the following detailed description of the preferred embodiments thereof in connection with the attached drawings.

BRIEF DESCRIPTION OF THE DRAWINGS

The foregoing and other features of several embodiments are described with reference to the drawings. In the drawings, the same components have the same reference numerals. The illustrated embodiments are intended to illustrate but not limit the invention. The drawings include the following Figures.

DETAILED DESCRIPTION

To facilitate an understanding of the adaptive aspects of the present disclosure, an exemplary MEMS device with an isolation structure is described. The specific construction and operation of the adaptive aspects of the isolation structure of the present disclosure are described with reference to the exemplary MEMS device.

Figure 1:
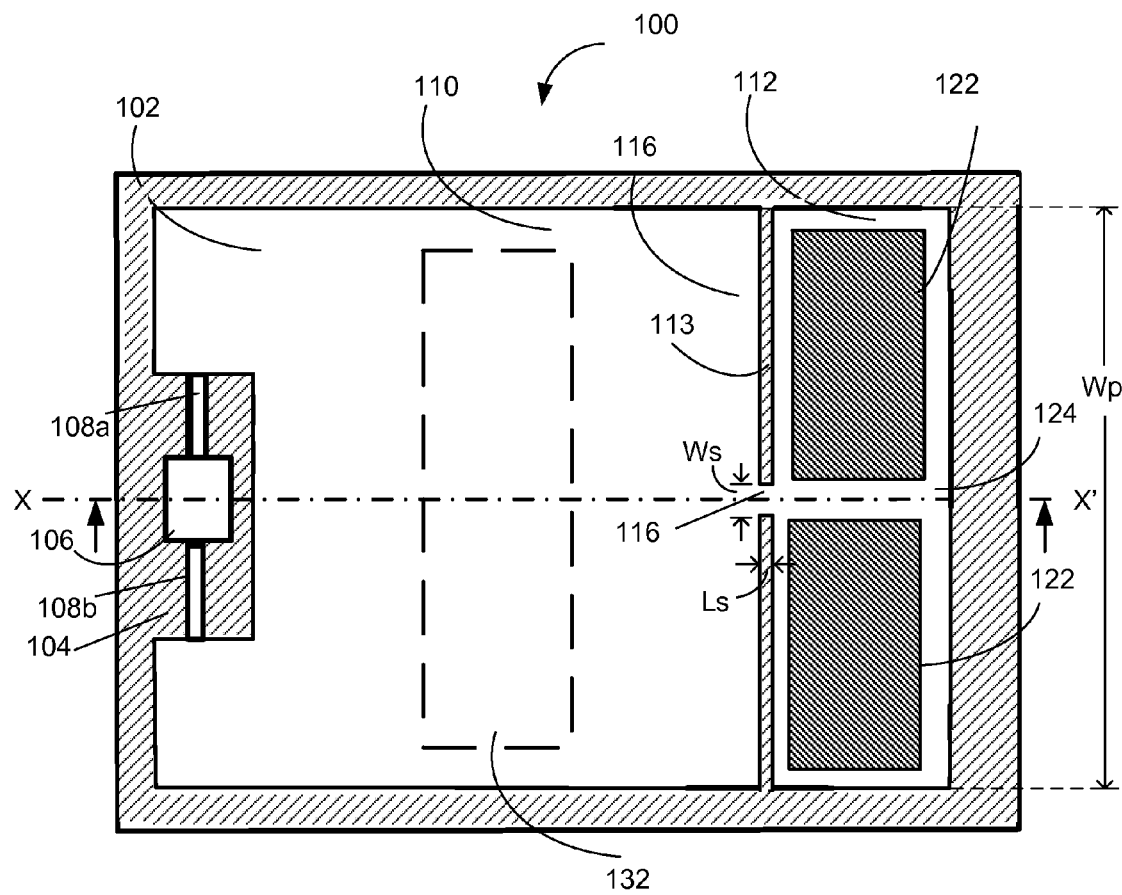
FIG. 1 shows top view of a MEMS device, according to one aspect of the present disclosure.

FIG. 1 shows a MEMS device 100, in accordance with an embodiment of this disclosure. The MEMS device 100 includes a free layer 102, a underlying substrate 104 and an anchor 106 disposed over the underlying substrate 104. A pair of springs 108a and 108b couple the free layer 102 to the anchor 106, such that free layer 102 is movable relative to the underlying substrate 104.

Free layer 102 includes a first portion 110 and a second portion 112. A stem 116 couples the first portion 110 to the second portion 112. In some examples, the stem 116 couples first portion 110 to the second portion 112, along a first side 113. For example, stem 116 couples the first portion 110 to the second portion 112, along the first side 113. The stem 116 acts as a stress-isolation structure by allowing second portion 112 to deform independent of the first portion 110. Sometimes, stem 116 may be referred to as a stress-isolation structure.

One or more strips of sense materials 122 are disposed over the second portion 112. Adjacent strips of sense materials are separated by a non-material portion 124. In some examples, pairs of adjacent strips of sense materials are disposed over the paddle such that the non-material portion extends along a length of the stem that couples the second portion to the first portion. As an example, referring to stem 116, adjacent strips of sense materials 122 and non-material portion 124, we notice that the non-material portion 124 extends along a length of the stem 116. For example, line X-X' passes along the length of the stem 116 and along the non-material portion 124.

The width Ws of the stem (in the Y direction) is typically less than ⅕ of the width Wp of the second portion in the same direction. The length Ls of the stem (in the X direction) is typically ½ to 2 times the width Ws of the stem. Typically, width Ws may be in the range of about 3 micrometers to about 10 micrometers. Typically, the length Ls may be in the range of about 2 micrometers to about 10 micrometers.

Figure 1A:
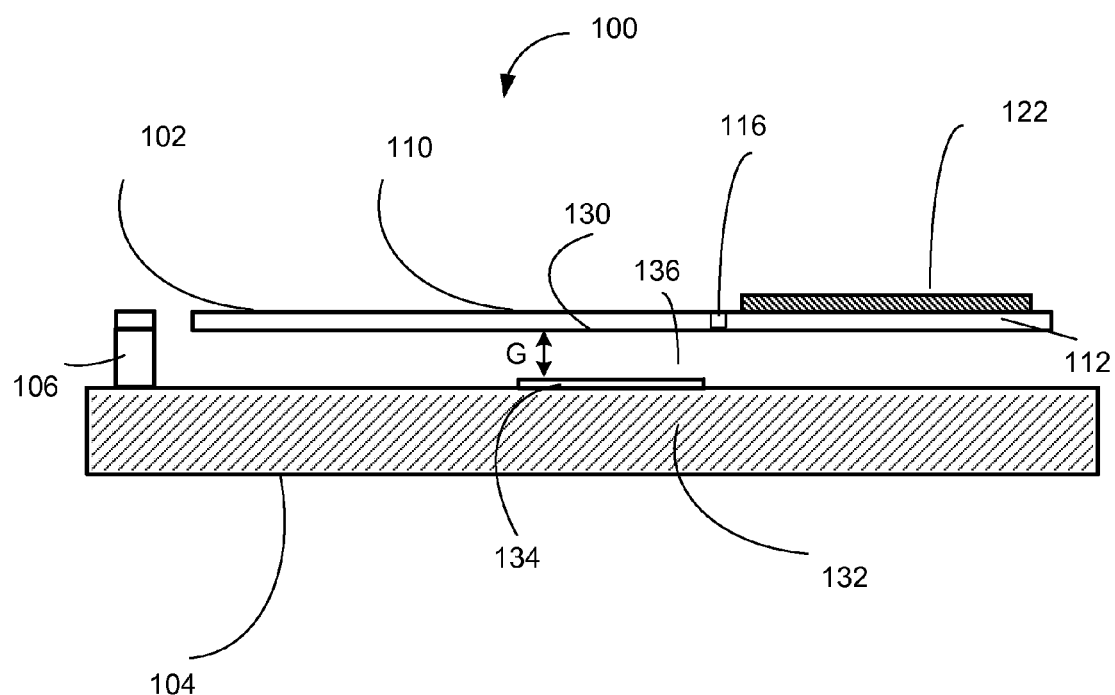
FIG. 1A shows a cross-sectional view of the MEMS device of FIG. 1, along an axis X-X', according to one aspect of the present disclosure.

Now, referring to FIG. 1A, MEMS device 100 will be further described. FIG. 1A shows a cross-sectional view of the MEMS device 100 of FIG. 1, along an axis X-X'. FIG. 1A shows that free layer 102 and underlying substrate 104 are separated by a gap. In some examples, sense materials react to an external force or influence and cause the free layer to move relative to the underlying substrate, thereby changing the gap G. Change in the gap is measured to determine the type and/or extent of the external influence.

In some examples, change in the gap is measured by constructing a sensor that is sensitive to the change in the gap. For example, a capacitor may be constructed, whose capacitance changes with change in the gap. As an example, a portion of the first portion 110 of the free layer 102 may be configured as a first electrode 130. The underlying substrate 104 includes a third portion 132. A second electrode 134 is disposed over a portion of the third portion 130, such that the first electrode 130 and second electrode 134 define two electrodes of a capacitor 136. The gap G between the electrodes form a dielectric layer (for example, with air or vacuum as a dielectric) for the capacitor 136. When the free layer 102 moves relative to the underlying substrate 104, the gap G between the first electrode 130 and second elector 134 changes, thereby changing the capacitance value of the capacitor 136. This change in the capacitance value of the capacitor 136 may be measured to determine the type and/or extent of the external force or influence.

Figure 1B:
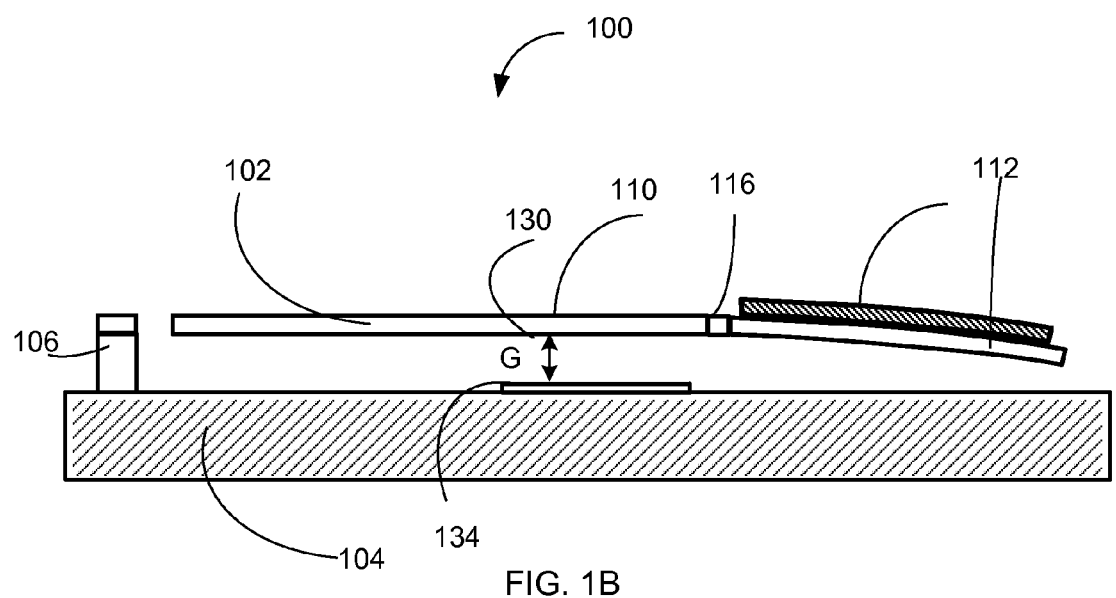
FIG. 1B shows a cross-sectional view of the MEMS device of FIG. 1, along an axis X-X', subjected to a stress on second portion of the free layer.

As one skilled in the art appreciates, in some sensor structures, the sense material 122 may have residual stress from a deposition process or from a temperature change after deposition. Compressive stress in the sense material 122 may be caused by the sense material 122 expanding faster than the substrate material, for example, material of free layer 102, as the temperature raises. Tensile stress is caused by the sense material 122 expanding more slowly. If the sense material 122 is under compressive stress, it causes the free layer to bend downwards. Most of the bending of the free layer is in the vicinity of the sense material 122, for example, in the second portion of the free layer. As the first portion and second portion of the free layer are coupled by a stem 116, when the sense material 122 expands, the second portion of the free layer bends, but the first portion of the free layer substantially remains flat. Stem 116 acts as a stress isolation structure. For example, FIG. 1B shows a cross sectional view of the MEMS device 100, along the axis X-X', with bent second portion 112 of the free layer 102. However, first portion 110 of the free layer 102 is substantially flat, thereby maintaining the gap G between the first electrode 130 and the second electrode 134 substantially constant.

As one skilled in the art appreciates, free layer may be a substrate, for example, a silicon substrate. Underlying substrate may be a silicon substrate. In some embodiments, one or more electronic circuits, for example, semiconductor circuits may be formed over the underlying substrate, by appropriate deposition techniques.

Figure 2:
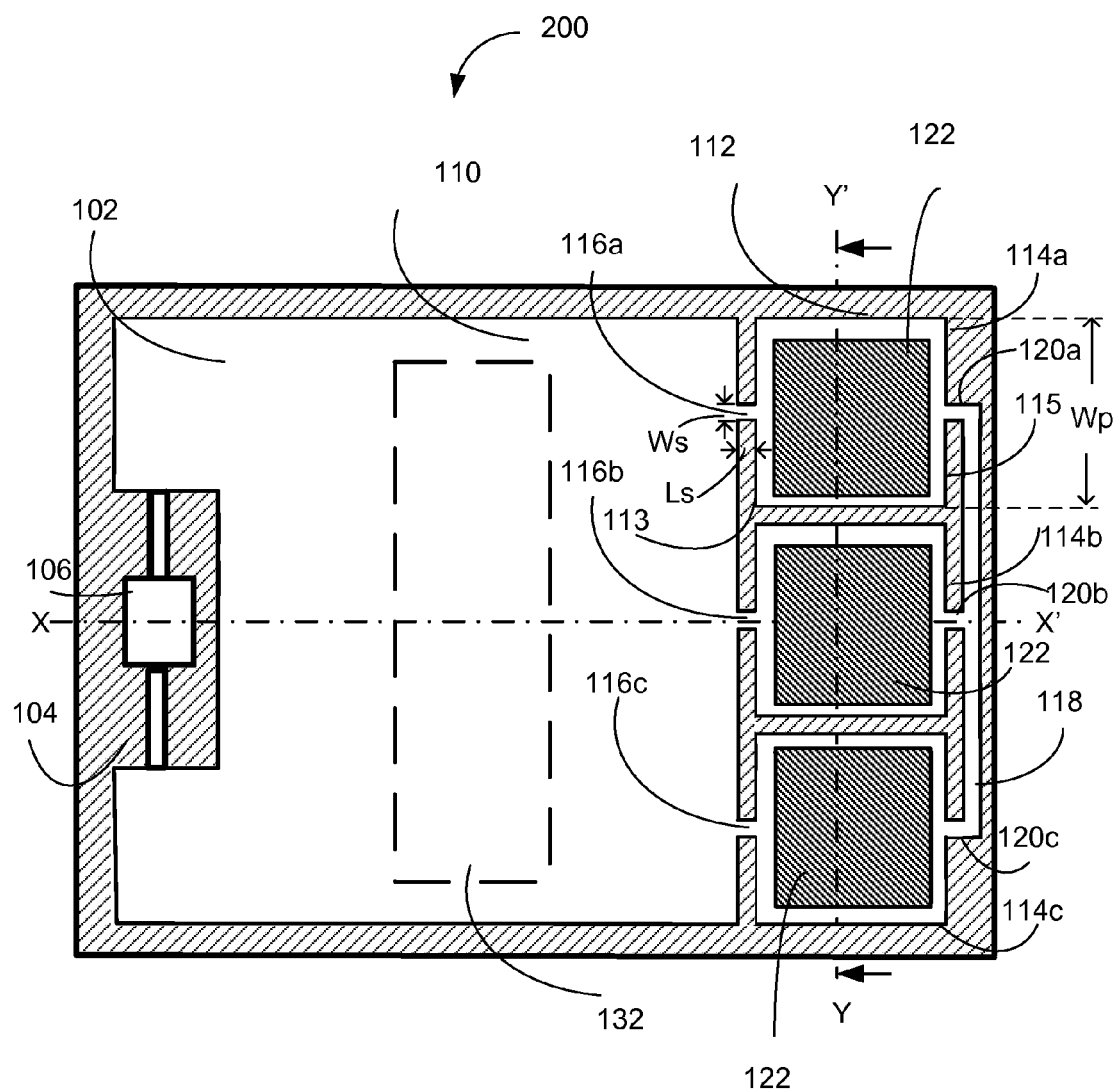
FIG. 2 shows an alternate top-view example of the MEMS device, according to one aspect of the present disclosure.

Now, referring to FIG. 2, another example embodiment of a MEMS device, for example, MEMS device 200 is disclosed. The MEMS device 200 may be similar to MEMS device 100. However, in the MEMS device 200, the second portion 112 of free layer 102 includes one or more paddles 114a-114c. One or more stems couple the first portion 110 to the second portion 112. In some examples, the stems couple first portion 110 to the second portion 112, along a first side 113. For example, stem 116a couples the first portion 110 to paddle 114a, along the first side 113. Similarly, stem 116b couples the first portion 110 to paddle 114b, along the first side 113 and stem 116c couples the first portion 110 to paddle 114c, along the first side 113. Sense material 122 is disposed over the second portion 112. For example, sense material 122 is disposed over the paddles 114a-114c.

The width Ws of the stem (in the Y direction) is typically less than ⅕ of the width Wp of the corresponding paddle in the same direction. The length Ls of the stem (in the X direction) is typically ½ to 2 times the width Ws of the stem. Typically, width Ws may be in the range of about 3 micrometers to about 10 micrometers. Typically, the length Ls may be in the range of about 2 micrometers to about 10 micrometers.

In some examples, the MEMS device 200 includes a paddle connector 118. One or more connector stems couple the paddle connector to the second portion 112. In some examples, the connector stems couple the paddle connector to the second portion 112, along a second side 115, which is opposite to the first side 113. For example, connector stem 120a couples the paddle connector 118 to paddle 114a, along the second side 115. Similarly, connector stem 120b couples the paddle connector 118 to paddle 114b, along the second side and connector stem 120c couples the paddle connector 118 to paddle 114c, along the second side 115. The paddle connector 118 forces the paddles 114a-114c to move together, for example, if a force is applied along a direction shown by line Y-Y'. This prevents the paddles 114a-114c from colliding with each other, due to for example an external force.

In some examples, the connector stem that couples the paddle to the paddle connector and the stem that couples the paddle to the first portion are disposed substantially along an axis passing through the length of the stem. For example, stem 116b that couples the paddle 114b to first portion 110 and connector stem 120b that couples the paddle 114b to paddle connector 118 is disposed substantially along an axis represented by the line X-X', which passes along the length of the stem 116b.

Figure 2A:
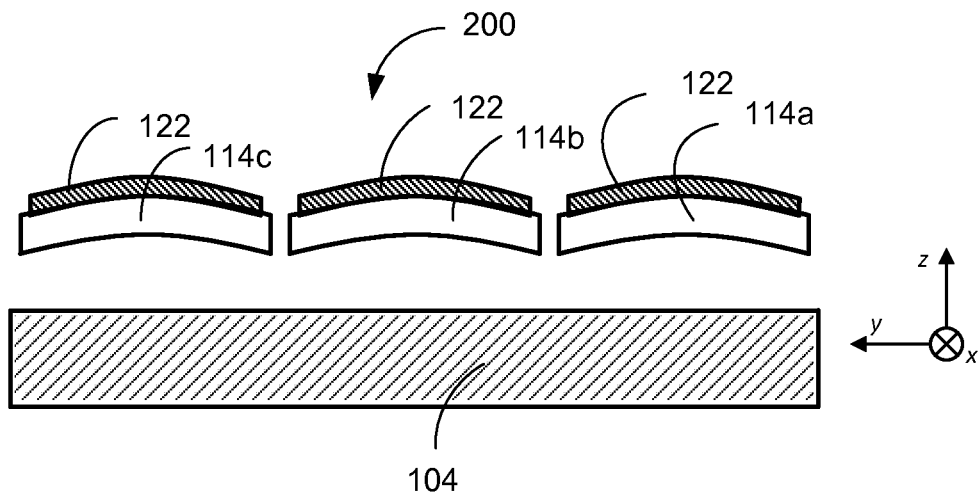
FIG. 2A shows a cross-sectional view of the MEMS device of FIG. 2, along an axis Y-Y', according to one aspect of the present disclosure.

Now, referring to FIG. 2A, a cross-sectional view of the MEMS device 200, along the axis Y-Y' is shown. FIG. 2A shows that the paddles 114a-114c are bent, for example, due to compressive residual stress from the deposition process or from a temperature change after deposition of the sense material 122. However, due to the isolation of the first portion and the second portion, the first portion of the free layer remains substantially flat, even though the second portion may bend.

Figure 3:
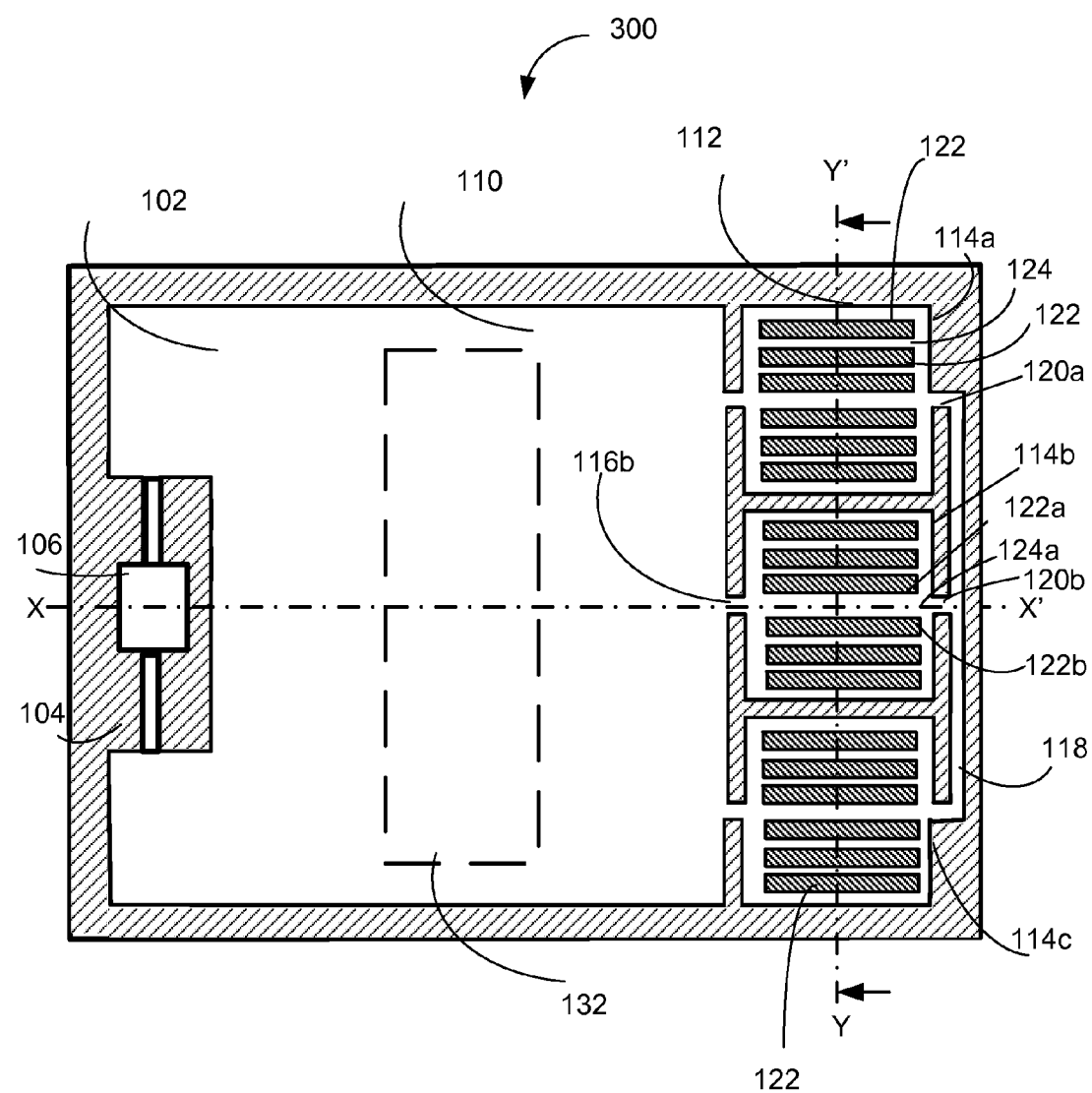
FIG. 3 shows yet another alternate example of MEMS device, according to one aspect of the present disclosure.

Now, referring to FIG. 3, yet another example of a MEMS device, for example, MEMS device 300 is disclosed. MEMS device 300 is similar to MEMS device 200. However, in this example, one or more strips of sense material 122 are disposed over the second portion 112. For example, one or more strips of sense material 122 are disposed over the paddles 114a-114c. Adjacent strips of sense materials are separated by a non-material portion 124. In some examples, pairs of adjacent strips of sense material are disposed over the paddle such that the non-material portion extends along a length of the stem that couples the paddle to the first portion. As an example, referring to paddle 114b, stem 116b, adjacent strips of sense materials 122a and 122b and non-material portion 124a, we notice that the non-material portion 124a extends along a length of the stem 116b. For example, line X-X' passes along the length of the stem 116b and along the non-material portion 124a.

In this example, as previously described with reference to MEMS device 200, MEMS device 300 includes a paddle connector 118 that is coupled to paddles 114a-114c through one or more connector stems. The connector stem that couples the paddle to the paddle connector and the stem that couples the paddle to the first portion are disposed substantially along an axis passing through the length of the stem. For example, stem 116b that couples the paddle 114b to first portion 110 and connector stem 120b that couples the paddle 114b to paddle connector 118 is disposed substantially along an axis represented by the line X-X', which passes along the length of the stem 116b. As one skilled in the art appreciates, the non-material portion 124a is also disposed along the same axis represented by line X-X'.

Figure 3A:
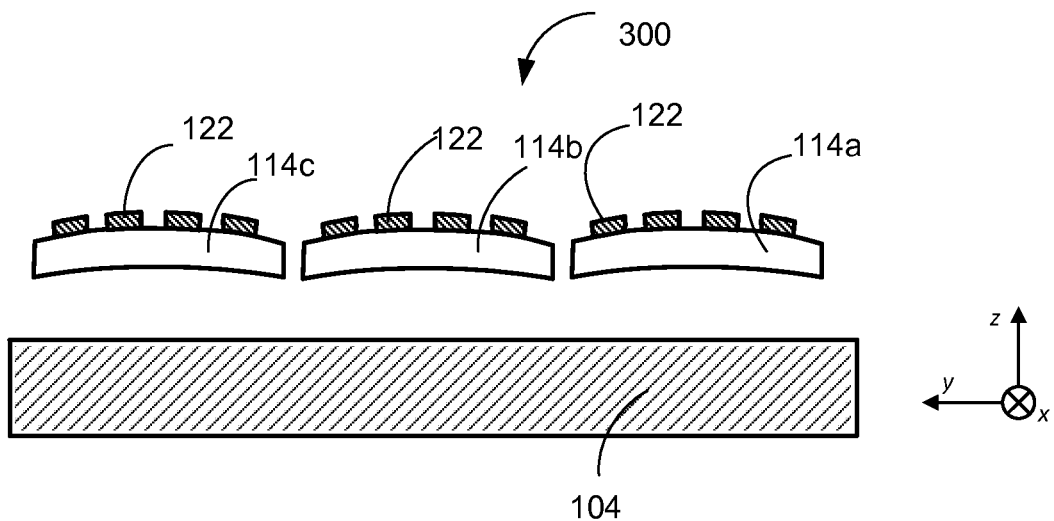
FIG. 3A shows a cross-sectional view of the MEMS device of FIG. 3, along an axis Y-Y', according to one aspect of the present disclosure.

Now, referring to FIG. 3A, a cross-sectional view of the MEMS device 300, along the axis Y-Y' is shown. FIG. 3A shows that the paddles 114a-114c are bent, for example, due to residual stress from the deposition process or from a temperature change after deposition of the sense material 122. However, due to the isolation of the first portion and the second portion, the first portion of the free layer remains substantially flat, even though the second portion may bend.

Example Sensor Implementations:

A MEMS device described in this disclosure may be configured to perform as a sensor, based upon appropriate selection and configuration of the sense material that reacts to an external force or influence. In one example, the sense material may be configured as a permanent magnet and the MEMS device may be configured as a magnetic sensor, to sense an external magnetic field that selectively moves the free layer with reference to underlying substrate. An example MEMS device configured as a magnetic sensor is described with reference to FIG. 4.

Figure 4:
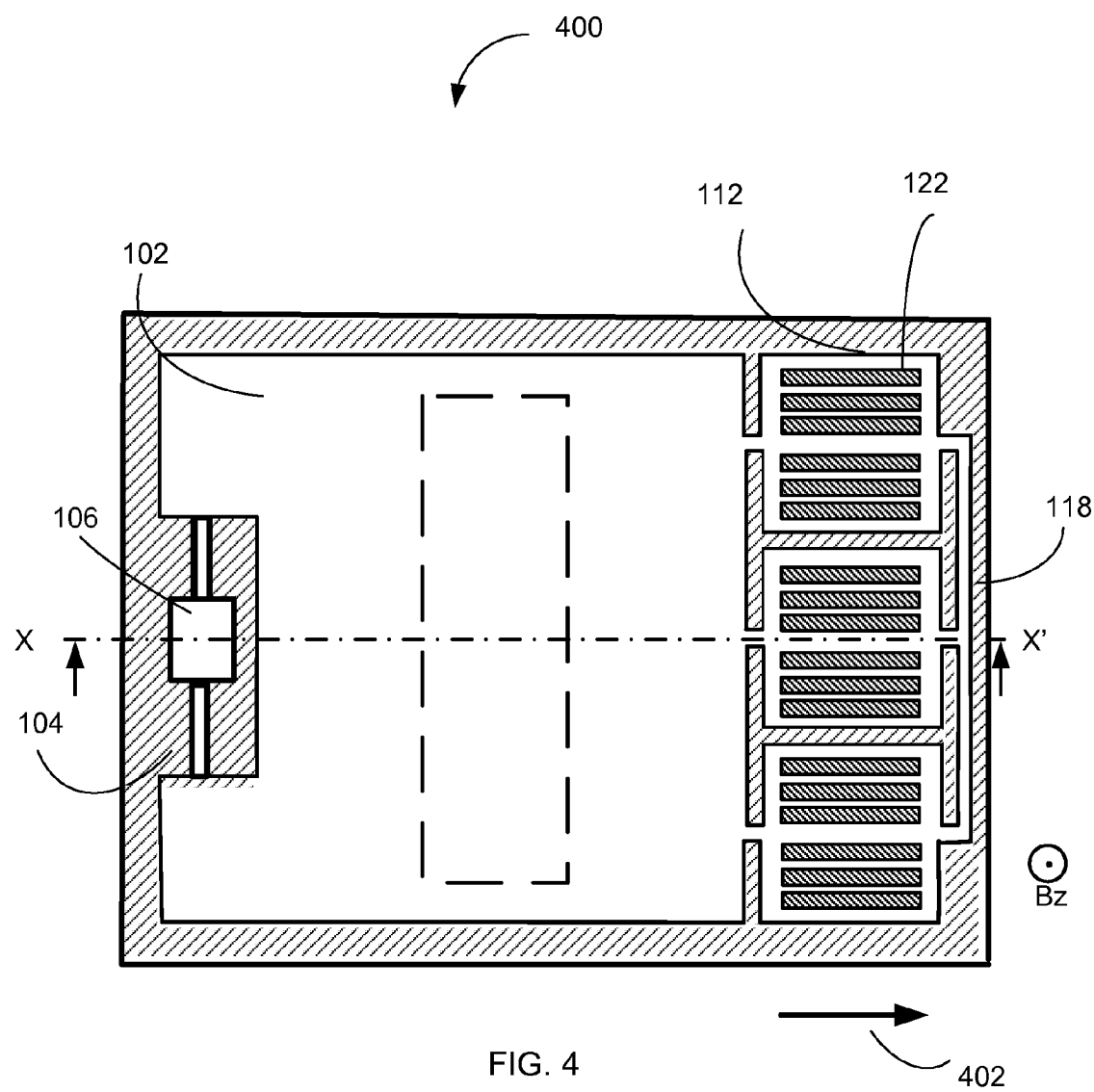
FIG. 4 shows an example top view of a MEMS device configured as a magnetic sensor, according to one aspect of the present disclosure.

Now, referring to FIG. 4, a MEMS device 400 configured as a magnetic sensor is described. The MEMS device 400 may be similar to MEMS device 300. The sense material 122 disposed over the second portion 112 of free layer 102 of MEMS device 400 is configured as permanent magnets. For example, strips of sense materials 122 may be configured as permanent magnets oriented along an axis shown by arrow 402. In one example, this axis corresponds to the X axis, as shown by line X-X'. With the permanent magnets oriented along the X axis, any change in an external magnetic field along the Z axis (which is orthogonal to the X-axis and shown as magnetic field Bz) will move the free layer with reference to the underlying substrate. This movement of the free layer 102 with reference to the underlying substrate 104 changes the gap between the first electrode and the second electrode of the MEMS device 400, as previously described with reference to MEMS device 300. As previously described, a change in the gap can be measured by measuring the change in the capacitance value of the sense capacitor. As one skilled in the art appreciates, the sense material 112 may be a metal or a metal alloy that may be magnetized as a permanent magnet. Some possible sense materials are samarium-cobalt (SmCo) or neodymium-iron-boron (NdFeB) alloys; or cobalt-iron (CoFe) or nickel-iron (NiFe) alloys with magnetic pinning layers situated above and below to create permanent magnets.

Figure 4A:
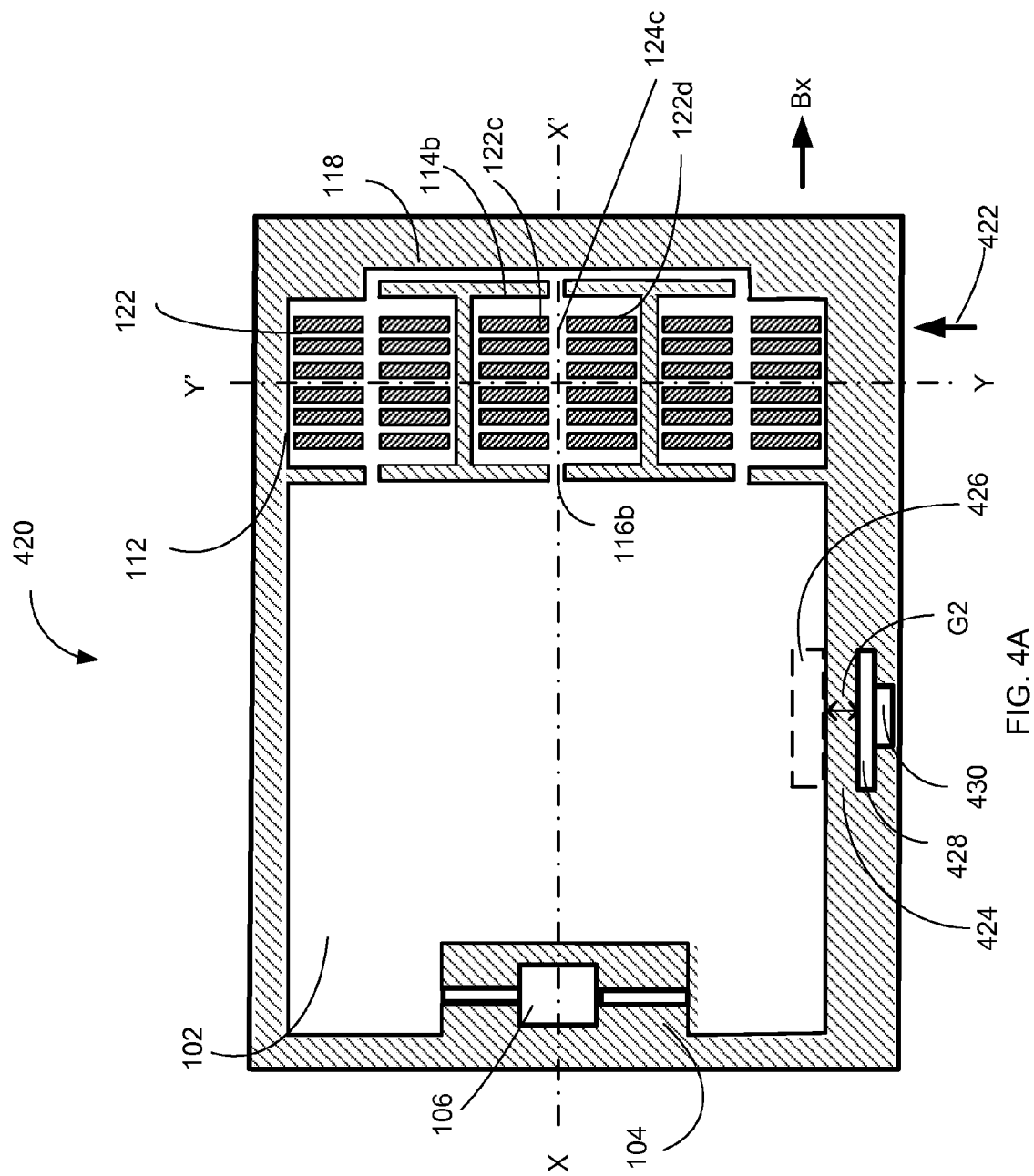
FIG. 4A shows another example top view of a MEMS device configured as a magnetic sensor, according to one aspect of the present disclosure.

Now, referring to FIG. 4A, another example MEMS device 420 configured as a magnetic sensor is described. The MEMS device 420 may be similar to MEMS device 400. However, the sense material 122 disposed over the second portion 112 of free layer 102 of MEMS device 420 is oriented in a different direction. In some examples, pairs of adjacent strips of sense material are disposed over the paddle such that the non-material portion extends along a length of the stem that couples the paddle to the first portion. As an example, referring to paddle 114b, stem 116b, adjacent strips of sense materials 122c and 122d and non-material portion 124b, we notice that the non-material portion 124c extends along a length of the stem 116b. For example, line X-X' passes along the length of the stem 116b and along the non-material portion 124c.

The sense material 122 is configured as permanent magnets. For example, strips of sense materials 122 may be configured as permanent magnets oriented along an axis shown by arrow 422. In one example, this axis corresponds to the Y axis, as shown by line Y-Y'. With the permanent magnets oriented along the Y axis, any change in an external magnetic field along the X axis (which is orthogonal to the Y-axis and shown as magnetic field Bx) will move the free layer with reference to the underlying substrate. However, this movement of the free layer with reference to the underlying substrate will be in-plane with reference to the underlying substrate.

A second sense capacitor 424 with a third electrode 426 and a fourth electrode 428 may be configured to measure this movement, by measuring a change in a gap G2 between the third electrode 426 and the fourth electrode 428. For example, the third electrode 426 may be formed on the free layer 104 and the fourth electrode 428 may be formed on the underlying substrate 104. For example, the fourth electrode 428 may be formed over a second anchor 430 disposed over the underlying substrate 104. And, the third electrode 426 is disposed over the free layer 102 such that any in-plane movement of the free layer 102 changes the gap G2.

For example, with the permanent magnets oriented along the Y axis, any change in an external magnetic field along the X axis (which is orthogonal to the Y-axis and shown as magnetic field Bx) will move the free layer with reference to the underlying substrate. This movement of the free layer 102 with reference to the underlying substrate 104 changes the gap G2 between the third electrode and the fourth electrode of the MEMS device 420. As previously described, a change in the gap can be measured by measuring the change in the capacitance value of the second sense capacitor.

As one skilled in the art appreciates, the sense material 112 may be a metal or a metal alloy that may be magnetized as a permanent magnet. Some possible materials are samarium-cobalt (SmCo) or neodymium-iron-boron (NdFeB) alloys; or cobalt-iron (CoFe) or nickel-iron (NiFe) alloys with magnetic pinning layers situated above and below to create permanent magnets.

Figure 5:
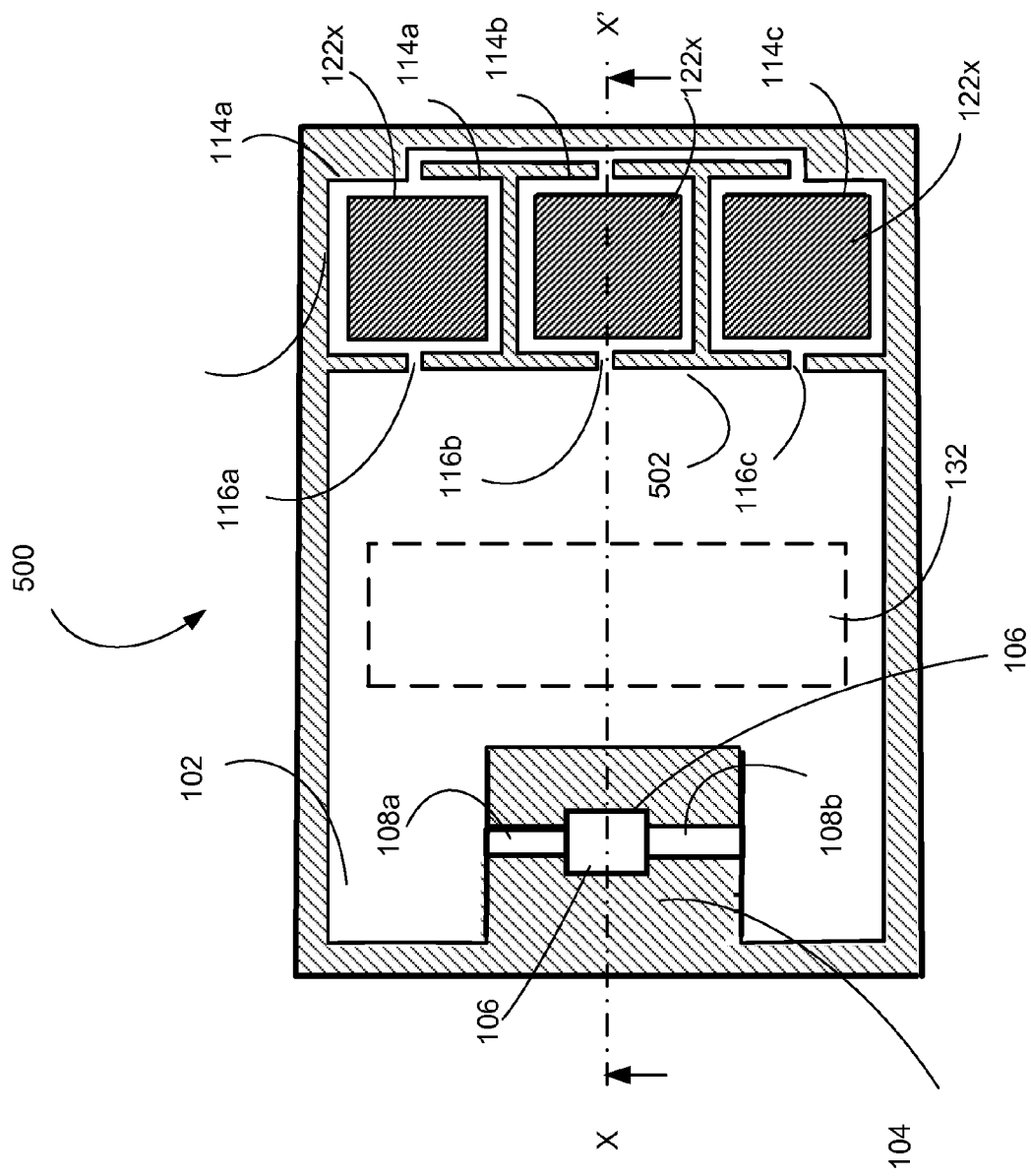
FIG. 5 shows an example top view of a MEMS device configured as an acceleration sensor, according to one aspect of the present disclosure.
Figure 5A:
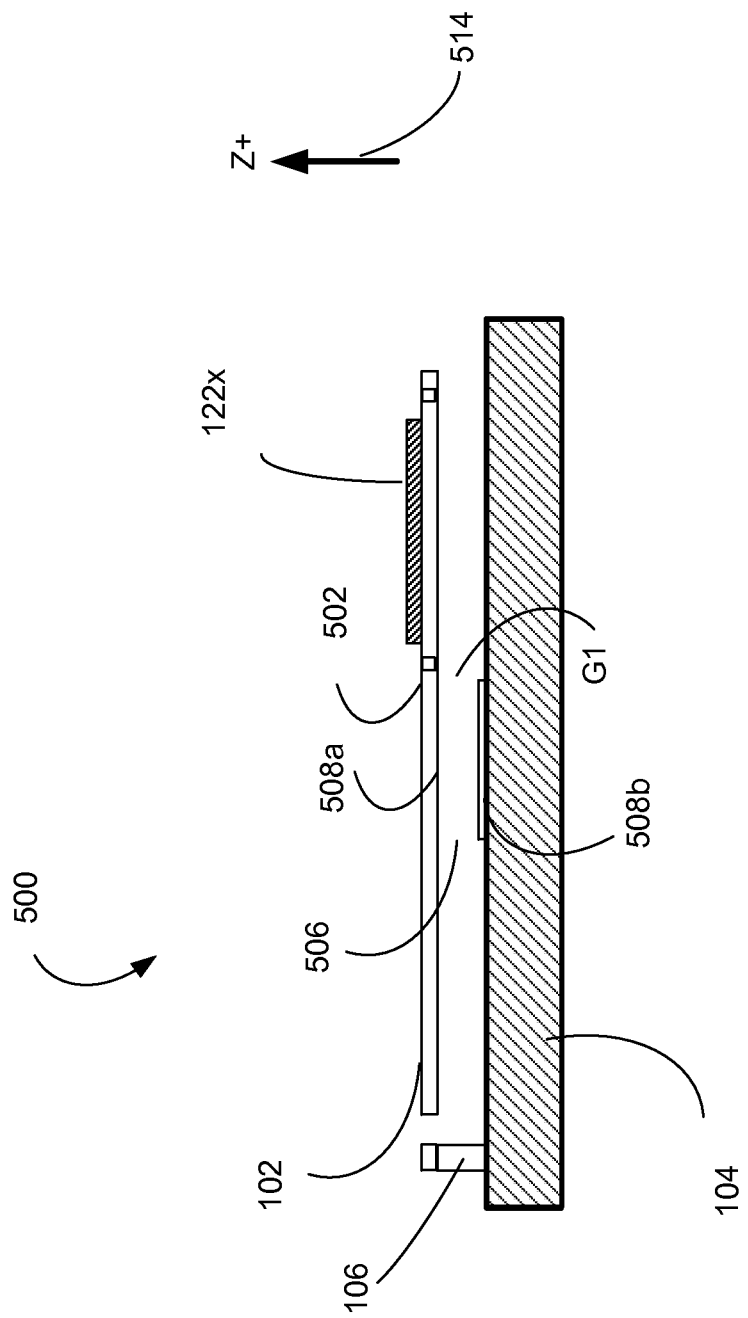
FIG. 5A shows a cross-sectional view of the MEMS device of FIG. 5, according to one aspect of the present disclosure.

Now, referring to FIGS. 5 and 5A, a MEMS device may be configured as an acceleration sensor. An example MEMS device 500 configured as a Z axis acceleration sensor is described with reference to FIGS. 5 and 5A. The construction of the MEMS device 500 is similar to the construction of the MEMS device 200. The MEMS device 500 includes a free layer 102, a underlying substrate 104 and an anchor 106 disposed over the underlying substrate 104. A pair of springs 108a and 108b couple the free layer 102 to the anchor 106, such that free layer 102 is movable relative to the underlying substrate 104. A set of paddles 114a-114c are formed at a first end 502 of the free layer 102. The set of paddles 114a-114c are coupled to the first end 502 of the free layer 102 by a plurality of stems 116a-116c. Further, a set of sense materials 122x are disposed over the first set of paddles 114a-114c.

FIG. 5A shows a cross-sectional view of the MEMS device 500, along a line X-X' shown in FIG. 5. Now, referring to FIG. 5A, a sense capacitor 506 is formed by a pair of electrodes 508a and 508b. The sense material 122x add weight to the free layer 102 at the end of the free layer 102.

When the MEMS device 500 is moved along a positive Z axis, as shown by arrow 514, for example, due to an external force, the first end 502 of the free layer 102 tilts towards the underlying substrate 104. This tilt causes a first gap G1 between the first pair of electrodes 508a and 508b to reduce, thereby increasing the capacitance value of the first sense capacitor 506. This change in the capacitance value of the first sense capacitor 506 may be measured to measure acceleration in the Z direction of the acceleration of the MEMS device 500. As one skilled in the art appreciates, the first sense material 122x may be a metal or a metal alloy. Some possible materials are tungsten, gold, iridium, osmium, or any other high-density material.

Figure 6:
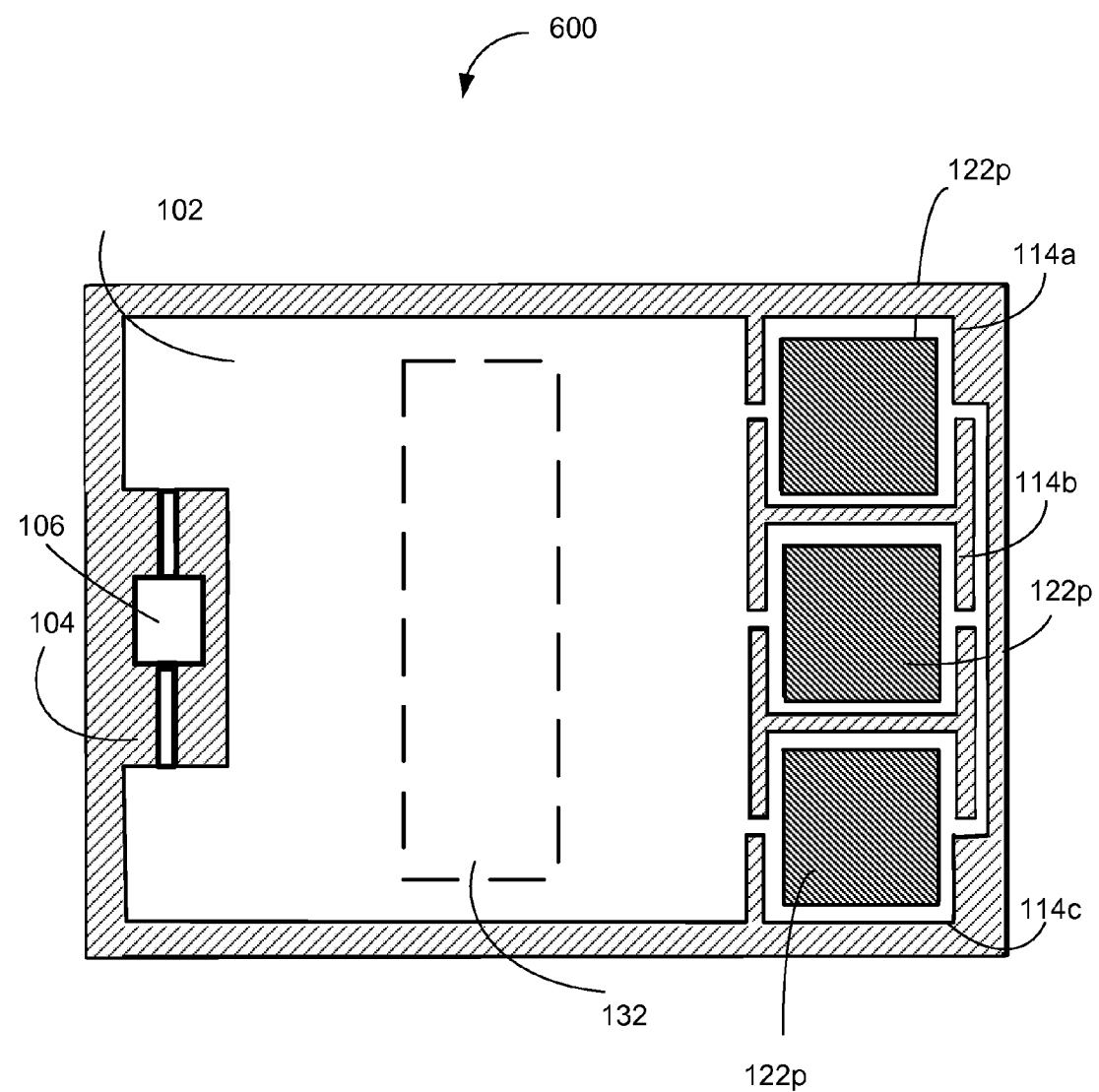
FIG. 6 shows an example top view of a MEMS device configured as a resonant sensor, according to one aspect of the present disclosure.

Now, referring to FIG. 6, MEMS device 600 may be configured as a chemical sensor. Sometimes, the chemical sensor may be referred to as a resonant sensor. The MEMS device 600 may be similar to MEMS device 200. For example, the sense material 122p disposed over paddles 114a-114c may be configured to absorb an external material, which would slightly increase the mass of the sense material 122p. In a resonating sensor, this increase in mass of the sense material 122p may cause the free layer 102 to resonate at a lower frequency. The external material may be a fluid. In some examples, the external material may be a liquid. In some examples, the external material may be a gas. In some examples, based on the characteristics of the external material, the change in the gap between the first electrode and the second electrode may be different for different external materials, thereby giving different capacitance values. This difference in capacitance value, for example, may be used to determine the type of external material present. The sense material 122p may be a polymer that selectively absorbs a target chemical, such as water vapor.

In a different use of the sensing material, the sensing material may be an anti-sticking material, for example titanium nitride, silicon carbide, or octadecyltrichlorosilane (OTS). The anti-sticking material prevents sticking of the second portion to other portions of the device with which it may come in contact with.

While embodiments of the present invention are described above with respect to what is currently considered its preferred embodiments, it is to be understood that the invention is not limited to that described above. To the contrary, the invention is intended to cover various modifications and equivalent arrangements within the spirit and scope of the appended claims.

What is claimed is:

1. A MEMS device, comprising:
a free layer with a first portion and a second portion;
an underlying substrate, the free layer movably positioned relative to the underlying substrate,
wherein the first portion and the second portion of the free layer are coupled through at least one stress-isolation structure,
wherein a sense material is disposed over portions of the second portion,
wherein the second portion is divided into a plurality of paddles, with each paddle coupled to the first portion through at least one stress-isolation structure; and
wherein at least one of the paddles has a plurality of strips of sense material disposed over the paddle and a gap between a pair of adjacent strips define a non-material portion for the pair of adjacent strips.

2. The MEMS device of claim 1, wherein the sense material is selected from a group of metal, alloy of metal and a polymer.

3. The MEMS device of claim 1, wherein a width of the stress-isolation structure is less than ⅕ of a width of the second portion and a length of the stress-isolation structure is 0.5 to 2 times the width of the stress-isolation structure.

4. The MEMS device of claim 1, wherein one of the pairs of adjacent strips of sense material are disposed over the paddle such that the non-material portion extends along a length of the stress-isolation structure that couples the paddle to the first portion.

5. The MEMS device of claim 4, wherein the width of the stress-isolation structure is less than ⅕ of a width of the paddle.

6. The MEMS device of claim 4, wherein the width of the stress-isolation structure is less than or equal to the non-material portion.

7. A MEMS device, comprising:
a free layer with a first portion and a second portion;
an underlying substrate, the free layer movably positioned relative to the underlying substrate,
wherein the first portion and the second portion of the free layer are coupled through at least one stress-isolation structure,
wherein a sense material is disposed over portions of the second portion,
wherein the second portion is divided into a plurality of paddles, with each paddle coupled to the first portion through at least one stress-isolation structure
wherein a paddle connector with a plurality of connector stems couples at least a pair of paddles.

8. The MEMS device of claim 7, wherein the paddle connector includes a plurality of connector stems, with at least one connector stem configured to couple the paddle connector to each one of the pair of paddles.

9. The MEMS device of claim 8, wherein the connector stem that couples the paddle to the paddle connector and the stress-isolation structure that couples the paddle to the first portion are disposed on opposite sides of the paddle.

10. The MEMS device of claim 9, wherein the connector stem that couples the paddle to the paddle connector and the stress-isolation structure that couples the paddle to the first portion are disposed substantially along an axis passing through a length of the stress-isolation structure.

11. The MEMS device of claim 10, wherein at least one of the paddles has a plurality of strips of sense material disposed over the paddle and a gap between a pair of adjacent strips define a non-material portion for the pair of adjacent strips.

12. The MEMS device of claim 11, wherein one of the pairs of adjacent strips of sense material are disposed over the paddle such that the non-material portion extends along a length of the stress-isolation structure that couples the paddle to the first portion.

13. The MEMS device of claim 12, wherein a width of the stress-isolation structure is less than or equal to the non-material portion.

14. The MEMS device of claim 2, wherein the underlying substrate includes a third portion, wherein the first portion of the free layer and the third portion of the underlying substrate are configured to form a capacitor.

15. The MEMS device of claim 14, wherein a first electrode of the capacitor is disposed over a portion of the first portion and a second electrode of the capacitor is disposed over a portion of the third portion, wherein a change in a distance between the first electrode and the second electrode changes the capacitance value of the capacitor.

16. The MEMS device of claim 15, wherein the distance between the first electrode and the second electrode substantially remains constant due to a bending stress imposed on the second portion of the free layer.

17. The MEMS device of claim 16, wherein the bending stress is imposed due to a temperature change and/or a residual stress due to deposition.

18. The MEMS device of claim 2, wherein the MEMS device is configured as sensor.

19. The MEMS device of claim 18, wherein the sensor is an acceleration sensor.

20. The MEMS device of claim 18, wherein the sensor is a magnetic field sensor.

21. The MEMS device of claim 18, wherein the sensor is a resonant sensor.

22. A method for providing a MEMS device, comprising:
providing a free layer with a first portion and a second portion;
providing a underlying substrate, the free layer movably positioned relative to the underlying substrate, wherein the first portion and the second portion of the first substrate are coupled through at least one stress-isolation structure, wherein a metal or a metal alloy is disposed over portions of the second portion,
wherein the second portion is divided into a plurality of paddles, with each paddle coupled to the first portion through at least one stress-isolation structure, and
wherein at least one of the paddles has a plurality of strips of sense material disposed over the paddle and a gap between a pair of adjacent strips define a non-material portion for the pair of adjacent strips.

23. The method of claim 22, wherein the sense material is selected from a group of metal, metal alloy and a polymer.

24. The method of claim 22, wherein a width of the stress-isolation structure is less than ⅕ of a width of the second portion and a length of the stress-isolation structure is 0.5 to 2 times the width of the stress-isolation structure.

25. The method of claim 22, wherein one of the pairs of adjacent strips of sense material are disposed over the paddle such that the non-material portion extends along a length of the stress-isolation structure that couples the paddle to the first portion.

26. The method of claim 25, wherein the width of the stress-isolation structure is less than ⅕ of a width of the paddle.

27. The method of claim 25, wherein a width of the stress-isolation structure is less than or equal to the non-material portion.

28. A method for providing a MEMS device, comprising:
providing a free layer with a first portion and a second portion;
providing a underlying substrate, the free layer movably positioned relative to the underlying substrate, wherein the first portion and the second portion of the first substrate are coupled through at least one stress-isolation structure, wherein a metal or a metal alloy is disposed over portions of the second portion,
wherein the second portion is divided into a plurality of paddles, with each paddle coupled to the first portion through at least one stress-isolation structure, and
wherein a paddle connector with a plurality of connector stems couples at least a pair of paddles.

29. The method of claim 28, wherein the paddle connector includes a plurality of connector stems, with at least one connector stress-isolation structure configured to couple the paddle connector to each one of the pair of paddles.

30. The method of claim 29, wherein the connector stem that couples the paddle to the paddle connector and the stress-isolation structure that couples the paddle to the first portion are disposed on opposite sides of the paddle.

31. The method of claim 30, wherein the connector stem that couples the paddle to the paddle connector and the stress-isolation structure that couples the paddle to the first portion are disposed substantially along an axis passing through a length of the stress-isolation structure.

32. The method of claim 31, wherein at least one of the paddles has a plurality of strips of sense material disposed over the paddle and a gap between a pair of adjacent strips define a non-material portion for the pair of adjacent strips.

33. The method of claim 32, wherein one of the pairs of adjacent strips of sense material are disposed over the paddle such that the non-material portion extends along a length of the stress-isolation structure that couples the paddle to the first portion.

34. The method of claim 33, wherein a width of the stress-isolation structure is less than or equal to the non-material portion.

35. The method of claim 33, wherein the underlying substrate includes a third portion, wherein the first portion of the free layer and the third portion of the underlying substrate are configured to form a capacitor.

36. The method of claim 35, wherein a first electrode of the capacitor is disposed over a portion of the first portion and a second electrode of the capacitor is disposed over a portion of the third portion, wherein a change in a distance between the first electrode and the second electrode changes the capacitance value of the capacitor.

37. The method of claim 36, wherein the distance between the first electrode and the second electrode substantially remains constant due to a bending stress imposed on the second portion of the free layer.

38. The method of claim 37, wherein the bending stress is imposed due to a temperature change.

39. The method of claim 23, wherein the MEMS device is configured as sensor.

40. The method of claim 39, wherein the sensor is an acceleration sensor.

41. The method of claim 39, wherein the sensor is a magnetic field sensor.

42. The method of claim 39, wherein the sensor is a resonant sensor.

43. The method of claim 22, wherein the sense material is an anti-sticking material.

44. The method of claim 23, wherein the underlying substrate includes a third portion, wherein the first portion of the free layer and the third portion of the underlying substrate are configured to form a capacitor.

45. The method of claim 44, wherein a first electrode of the capacitor is disposed over a portion of the first portion and a second electrode of the capacitor is disposed over a portion of the third portion, wherein a change in a distance between the first electrode and the second electrode changes the capacitance value of the capacitor.

46. The method of claim 45, wherein the distance between the first electrode and the second electrode substantially remains constant due to a bending stress imposed on the second portion of the free layer.

47. The method of claim 46, wherein the bending stress is imposed due to a temperature change.

48. The MEMS device of claim 12, wherein the underlying substrate includes a third portion, wherein the first portion of the free layer and the third portion of the underlying substrate are configured to form a capacitor.

49. The MEMS device of claim 48, wherein a first electrode of the capacitor is disposed over a portion of the first portion and a second electrode of the capacitor is disposed over a portion of the third portion, wherein a change in a distance between the first electrode and the second electrode changes the capacitance value of the capacitor.

50. The MEMS device of claim 49, wherein the distance between the first electrode and the second electrode substantially remains constant due to a bending stress imposed on the second portion of the free layer.

51. The MEMS device of claim 50, wherein the bending stress is imposed due to a temperature change.

52. The MEMS device of claim 1, wherein a paddle connector with a plurality of connector stems couples at least a pair of paddles.

53. The MEMS device of claim 52, wherein the paddle connector includes a plurality of connector stems, with at least one connector stem configured to couple the paddle connector to each one of the pair of paddles.

54. The MEMS device of claim 53, wherein the connector stem that couples the paddle to the paddle connector and the stress-isolation structure that couples the paddle to the first portion are disposed on opposite sides of the paddle.

55. The MEMS device of claim 54, wherein the connector stem that couples the paddle to the paddle connector and the stress-isolation structure that couples the paddle to the first portion are disposed substantially along an axis passing through a length of the stress-isolation structure.

56. The MEMS device of claim 55, wherein at least one of the paddles has a plurality of strips of sense material disposed over the paddle and a gap between a pair of adjacent strips define a non-material portion for the pair of adjacent strips.

57. The MEMS device of claim 56, wherein one of the pairs of adjacent strips of sense material are disposed over the paddle such that the non-material portion extends along a length of the stress-isolation structure that couples the paddle to the first portion.

58. The MEMS device of claim 57, wherein a width of the stress-isolation structure is less than or equal to the non-material portion.

59. The method of claim 22, wherein a paddle connector with a plurality of connector stems couples at least a pair of paddles.

60. The method of claim 59, wherein the paddle connector includes a plurality of connector stems, with at least one connector stress-isolation structure configured to couple the paddle connector to each one of the pair of paddles.

61. The method of claim 60, wherein the connector stem that couples the paddle to the paddle connector and the stress-isolation structure that couples the paddle to the first portion are disposed on opposite sides of the paddle.

62. The method of claim 61, wherein the connector stem that couples the paddle to the paddle connector and the stress-isolation structure that couples the paddle to the first portion are disposed substantially along an axis passing through a length of the stress-isolation structure.

63. The method of claim 62, wherein at least one of the paddles has a plurality of strips of sense material disposed over the paddle and a gap between a pair of adjacent strips define a non-material portion for the pair of adjacent strips.

64. The method of claim 63, wherein one of the pairs of adjacent strips of sense material are disposed over the paddle such that the non-material portion extends along a length of the stress-isolation structure that couples the paddle to the first portion.

65. The method of claim 64, wherein a width of the stress-isolation structure is less than or equal to the non-material portion.

* * * * *